(12) United States Patent
Marte et al.

(10) Patent No.: US 9,515,045 B2
(45) Date of Patent: Dec. 6, 2016

(54) METHOD AND APPARATUS FOR INSPECTING A SEMICONDUCTOR CHIP PRIOR TO BONDING

(75) Inventors: Andreas Marte, Steinach (CH); Tim Oliver Stadelmann, Kreuzlingen (CH)

(73) Assignee: Kulicke and Soffa Die Bonding GmbH, Berg (CH)

( * ) Notice: Subject to any disclaimer, the term of this patent is extended or adjusted under 35 U.S.C. 154(b) by 829 days.

(21) Appl. No.: 13/558,771

(22) Filed: Jul. 26, 2012

(65) Prior Publication Data
US 2013/0025791 A1    Jan. 31, 2013

(30) Foreign Application Priority Data

Jul. 31, 2011 (CH) ........................ 1265/11

(51) Int. Cl.
| | | |
|---|---|---|
| B32B 37/00 | (2006.01) |
| H01L 23/00 | (2006.01) |
| H01L 21/66 | (2006.01) |
| G01N 29/04 | (2006.01) |
| H01L 21/67 | (2006.01) |

(52) U.S. Cl.
CPC ............ H01L 24/75 (2013.01); G01N 29/045 (2013.01); H01L 21/67132 (2013.01); H01L 21/67144 (2013.01); H01L 21/67253 (2013.01); H01L 22/12 (2013.01); G01N 2291/2697 (2013.01); H01L 2224/759 (2013.01); H01L 2224/75651 (2013.01); H01L 2224/75745 (2013.01); H01L 2224/75822 (2013.01); H01L 2924/12042 (2013.01); Y10T 156/17 (2015.01)

(58) Field of Classification Search
CPC ............ H01L 22/12; H01L 21/67132; H01L 21/67144; H01L 21/67253; H01L 24/75; G01N 29/045

USPC ............ 156/64, 73.1, 73.6, 378, 379, 580, 580.1,156/580.2; 264/64, 69
See application file for complete search history.

(56) References Cited

U.S. PATENT DOCUMENTS 5,972,782 A * 10/1999 Ostapenko .................... 438/488
6,413,789 B2    7/2002 Ostapenko
(Continued)

FOREIGN PATENT DOCUMENTS

WO    WO2011/018375    2/2011

OTHER PUBLICATIONS

Applied Physics Letters 88, 11907 (2006) "Crack detection and analyses using resonance ultrasonic vibrations in full-size crystalline silicon wafers"; A. Belyaev, O. Polupan, W. Dallas, S. Ostapenko, D. Hess, and J. Wohlgemuth.

(Continued)

Primary Examiner — James Sells
(74) Attorney, Agent, or Firm — Stradley Ronon Stevens & Young LLP

(57) ABSTRACT

A chip handling apparatus, unit and method is presented. The chip handling apparatus comprises a chip supply station; a chip mounting station; and one or more chip handling units configured to pick a chip from the supply station, transport the chip to the mounting station, and place the chip at a mounting location; wherein each chip handling unit is configured to temporarily retain the chip in a defined position relative to the chip handling unit. The chip handling apparatus further comprises means for inducing sonic vibrations in the chip when retained by one of the chip handling units; and means for measuring the vibrations induced in the chip.

13 Claims, 5 Drawing Sheets

(56) References Cited

U.S. PATENT DOCUMENTS 8,528,407 B2 * 9/2013 Ostapenko ............... 73/579
2010/0138027 A1 6/2010 Ostapenko

OTHER PUBLICATIONS

Measurement Science and Technology 18 (2007) 852-858 "Resonance ultrasonic vibrations for crack detection in photovoltaic silicon wafers"; W. Dallas, O. Polupan, and S. Ostapenko.

* cited by examiner

METHOD AND APPARATUS FOR INSPECTING A SEMICONDUCTOR CHIP PRIOR TO BONDING

CROSS-REFERENCE TO RELATED APPLICATION

This application claims the benefit of Swiss Patent Application No. 01265/11 filed Jul. 31, 2011, the content of which is incorporated herein by reference.

FIELD OF THE INVENTION

The present invention pertains to the field of automation technology. It relates to an apparatus, a unit, and a method for handling chips, in particular semiconductor dies, in accordance with the preamble of the independent patent claims.

BACKGROUND OF THE INVENTION

One of the biggest challenges in semiconductor packaging is picking, handling and processing of very thin semiconductor chips. The semiconductor chips are generally provided on a carrier tape, which generally contains a whole semiconductor wafer that has been cut into small chips, a process frequently referred to as dicing. The semiconductor chips are thus commonly referred to as dies. The carrier tape is often the same tape that supported the wafer during dicing, often referred to as dicing tape. Die thicknesses of down to 25 µm are common today, and there is an ongoing trend to decrease thicknesses even further. Thicknesses of 15 µm have already been anticipated on semiconductor manufacturer roadmaps.

Die bonders pick a single die from the carrier tape and place and subsequently attach the picked die onto a substrate or onto another die. In most situations, the die is attached permanently, but configurations where dies are only attached temporarily also exist. Often, a temporary attachment is subsequently turned into a permanent one by an additional heating and/or pressing process. Typically, thin dies come with a wafer backside lamination (WBL) or film over wire (FOW) lamination, i.e. an adhesive film which is applied to an unstructured side of the wafer or die. A process of thinning wafers, applying an adhesive film to the wafers, mounting the wafers to a carrier tape and frame, and dicing them into individual chips is usually referred to as wafer preparation. The lamination, which allows for the dies to be attached due to its adhesive properties, may be provided either between the carrier tape and the wafer, or on a surface of the wafer facing away from the carrier tape.

Picking, placing, and transport between pick and place locations may be carried out by a single chip handling unit in the die bonder. In modern die bonders, however, a plurality of chip handling units is often present: In general, picking takes place from a so called wafer table, and is assisted by a zeroth chip handling unit, also referred to as die ejector. The die ejector facilitates the removal of the die from the carrier tape, e.g. by pushing the die against a first chip handling unit called pick unit—from underneath the carrier tape. The pick unit subsequently picks the die from the carrier tape in a pick process and hands it over to a second chip handling unit, also referred to as place unit. The place unit places the die onto a target position, where it is attached. In some cases, at least one third chip handling unit—a so called transfer unit—is provided to hand the die from the pick unit to the place unit. An example is given in WO 07118511 A1 which is hereby incorporated by reference in its entirety. In this manner, a die may be attached to a substrate, e.g. a leadframe, printed circuit board, multilayer board etc., or to another die, which itself may be have been attached in the same way.

The fabrication of very thin wafers and the corresponding dies is very expensive as compared to standard thickness wafers without lamination. Sawing, picking as well as handling of very thin dies have significant yield losses. Most of the yield is lost during wafer preparation, die picking, or subsequent handling, resulting in damaged dies due to typical defects as e.g. broken dies, cracked dies, chipped dies, etc. Both place and attachment processes, in comparison, are more reliable, giving rise to only negligible loss.

In particular for stacked die bond processes where two or more dies are attached onto one another, attaching of a broken die may have dramatic consequences: If a damaged die is attached onto a stack, all previously attached dies in that stack—also referred to as package—are lost. In an extreme situation, for example, a package consisting of 15 stacked dies may thus be lost by attaching a broken 16th die on top of it. Assuming a pick process yield of 99%, an expected package yield drops to $0.99^{\wedge}16$, i.e. to 85% in this example, and to only 44% for a pick process yield of 95%.

Known inspection methods for detecting broken, cracked or chipped dies on die bonders are performed before the pick process—which itself has limited yield—and are generally based on imaging a die surface under surface illumination, followed by image processing. These inspection techniques have limited reliability due to low crack contrast and crack width, die warpage—also referred to as potato chip effect—and due to the interference of crack signatures with other similar looking patterns on the die surface.

Until recently, die bonders have not offered any mechanism or functionality to detect die cracks prior to the bond process and after the pick process. There were two main reasons for that: First, the typical "direct" pick & place architecture of die bonding machines does not allow for the usage of special (pick & place) tooling which incorporates means for die crack detection. Second, die cracks are hard to detect as their appearance varies extremely, both in shape, width etc.

In WO2011/018375 A1, a method and apparatus for inspecting a chip prior to bonding by means of an optical crack detection method was described.

SUMMARY OF THE INVENTION

It is thus an object of the invention to allow for an inspection after picking of a die rather than—or in addition to—one before picking of the die, e.g. on a die ejector, and thus guarantee that only undamaged dies are attached to a substrate or a previously attached die by a die bonder.

In addition, the invention shall allow for an identification of damaged dies before attach, and thus to allow for omitting to place such damaged dies onto a substrate or a stack of previously attached dies. Ideally, inspection of the die should be possible immediately before it is placed and subsequently attached to the substrate or to an already attached die.

The above objects are achieved by a chip handling apparatus and a process for handling a chip according to the independent claims.

In a chip handling apparatus and a method for handling a chip in accordance with the present invention, acoustic and/or ultrasonic vibrations are induced in a die, e.g. by means of an actuator, in particular a piezo electric actuator.

In a preferred embodiment of the method and apparatus in accordance with the invention, the die is centered on the actuator and temporarily attached by means of vacuum. As an excitation frequency, i.e. a vibration frequency of the actuator, is sweeped, eigenmodes of the die are excited. Eigenfrequencies corresponding to the eigenmodes may be characterized by a mode number, and typically range from a few 100 Hz to several 10 kHz, depending on die size, die thickness, etc.

In an exemplary embodiment of the present invention, a chip handling apparatus, in particular a die bonder, is presented which comprises a chip supply station; a chip mounting station; and one or more chip handling units configured to pick a chip from the supply station, transport the chip to the mounting station, and place the chip at a mounting location; wherein each chip handling unit is configured to temporarily retain the chip in a defined position relative to the chip handling unit, and wherein the chip handling apparatus further comprises means for inducing sonic vibrations in the chip when retained by one of the chip handling units; and means for measuring the vibrations induced in the chip.

In another exemplary embodiment of the present invention, a chip handling unit, in particular for use in a semiconductor die bonder, is presented, which is configured to receive a chip, in particular a semiconductor die, at a takeover location and to hand over said chip to a delivery location, said chip handling unit comprising, means for temporarily retaining the chip in a defined position relative to the chip handling unit, and means for inducing vibrations, in particular sonic and/or ultrasonic vibrations, in the chip.

In another exemplary embodiment of the present invention, a chip handling process, in particular for a die bonding process, is presented which comprises the steps of a) receiving a chip (5), in particular a semiconductor die, at a takeover location by means of chip handling unit; b) temporarily retaining the chip in a defined position relative to the chip handling unit; c) transporting the chip to a delivery location; and d) subsequently releasing the chip, wherein between steps a) and d), vibrations are induced in the chip; and a vibrations induced in the chip are measured.

The aforementioned and further objectives, advantages and features of the invention will be detailed in the description of preferred embodiments below in combination with the drawings.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
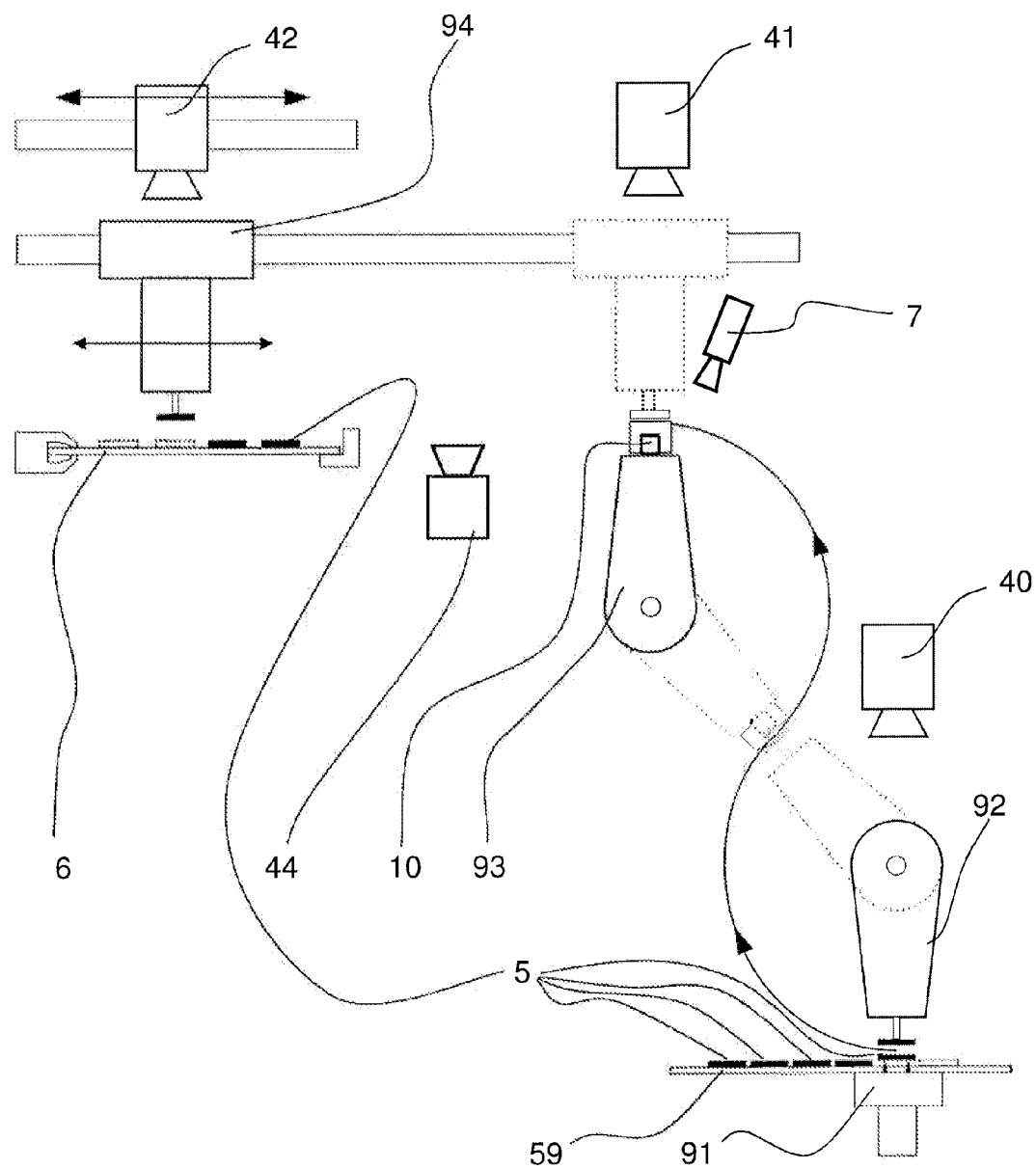
FIG. 1 shows a die bonder in accordance with an exemplary embodiment of the present invention.

FIG. 1 shows a schematic of an exemplary embodiment of a die bonder in accordance with the present invention. The die bonder comprises a plurality of chip handling units: A zeroth chip handling unit, also called die ejector 91, ejects a die 5, which may be laminated with a WBL or FOW lamination, from a carrier tape 59 at a wafer table. Wafer table and die ejector 91 act as chip supply station for die bonder. After the die 5 has been ejected, it is taken over by a first chip handling unit, also referred to as pick unit 92. The die bonder further comprises a second chip handling unit also referred to as place unit 94, for transporting die 5 to and placing it onto a target position on a substrate 6 at a chip mounting station. The pick unit 92 is capable of rotating around a first axis, and configured to hand the die 5 over to a third chip handling unit. Said third chip handling unit, also referred to as transfer unit 93, is capable of rotating about a second axis, and may thus hand the die 5 to the place unit 94. The transfer unit 93 comprises a chip handling tool 10, which comprises at least one vacuum orifice for temporarily attaching the die 5 to the chip handling tool 10. The transfer unit 93 further comprises a piezo electric actuator, which is configured to induce acoustic and/or ultrasonic vibrations in the die 5 attached to the chip handling tool 10. When the transfer unit 93 is at a delivery location as represented by a solid line in FIG. 1, acoustic and/or ultrasonic vibrations are induced in the die 5 by means of the piezo electric actuator. A laser displacement meter 7 is provided to measure the vibrations induced in die 5.

The die bonder further comprises a control system not shown in FIG. 1 to control the movements of the various chip handling units etc.

Figure 2:
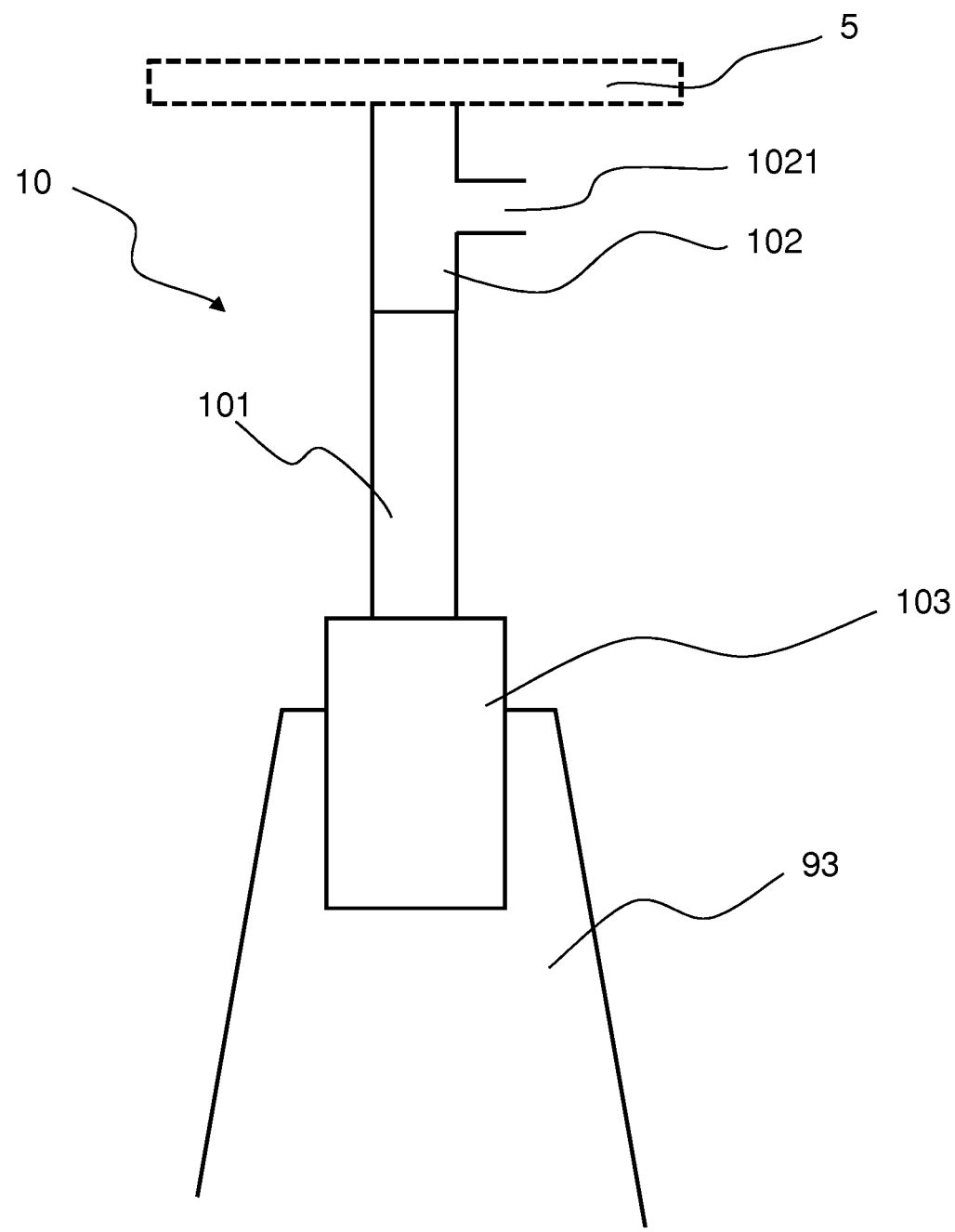
FIG. 2 shows a schematic of a preferred embodiment of a chip handling tool for use with the present invention.

FIG. 2 shows a schematic of a preferred embodiment of a chip handling tool 10 for use with the present invention. The chip handling tool 10 comprises a shank 103 by means of which it may e.g. be mounted to a chip handling unit, in particular the transfer unit 93. Piezo electric actuator 101 is provided on the shank 103. A tube 102 consisting of a flexible material, e.g. rubber, is mounted on the piezo electric acuator 101. The tube has a vacuum supply connection 1021, which allows for connecting to a vacuum source in order to temporarily retain die 5 sucked against a vacuum orifice formed at the top end of tube 102.

Figure 3:
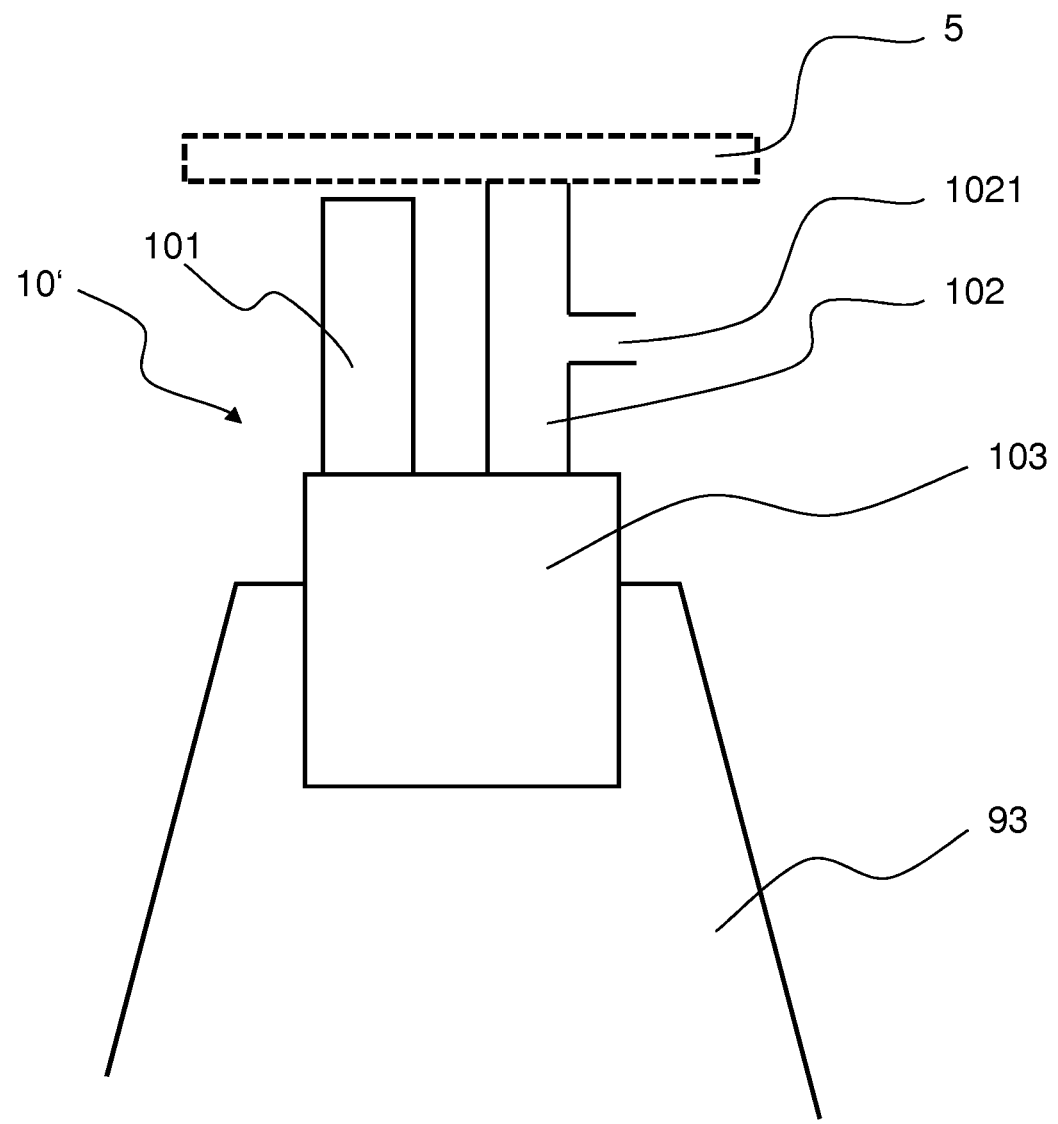
FIG. 3 shows a schematic of another preferred embodiment of a chip handling tool for use with the present invention.

FIG. 3 shows a schematic of another preferred embodiment of a chip handling tool 10' for use with the present invention. The chip handling tool 10' again comprises shank 103 by means of which it may e.g. be mounted to a chip handling unit, in particular the transfer unit 93. Piezo electric actuator 101 is again provided on the shank 103. In this embodiment, tube 102 is mounted directly on the shank 103. Again, die 5 may be sucked against the vacuum orifice formed at the top end of tube 102, and thus temporarily retained in position. Dimensions of tube 102 and piezo electric actuator 101 are chosen in such a way that a small air gap, preferably having a length between 25 and 500 µm, preferably 50 to 200 µm results between a die sucked against the top end of tube 102 and piezo electric actuator 101.

Figure 4:
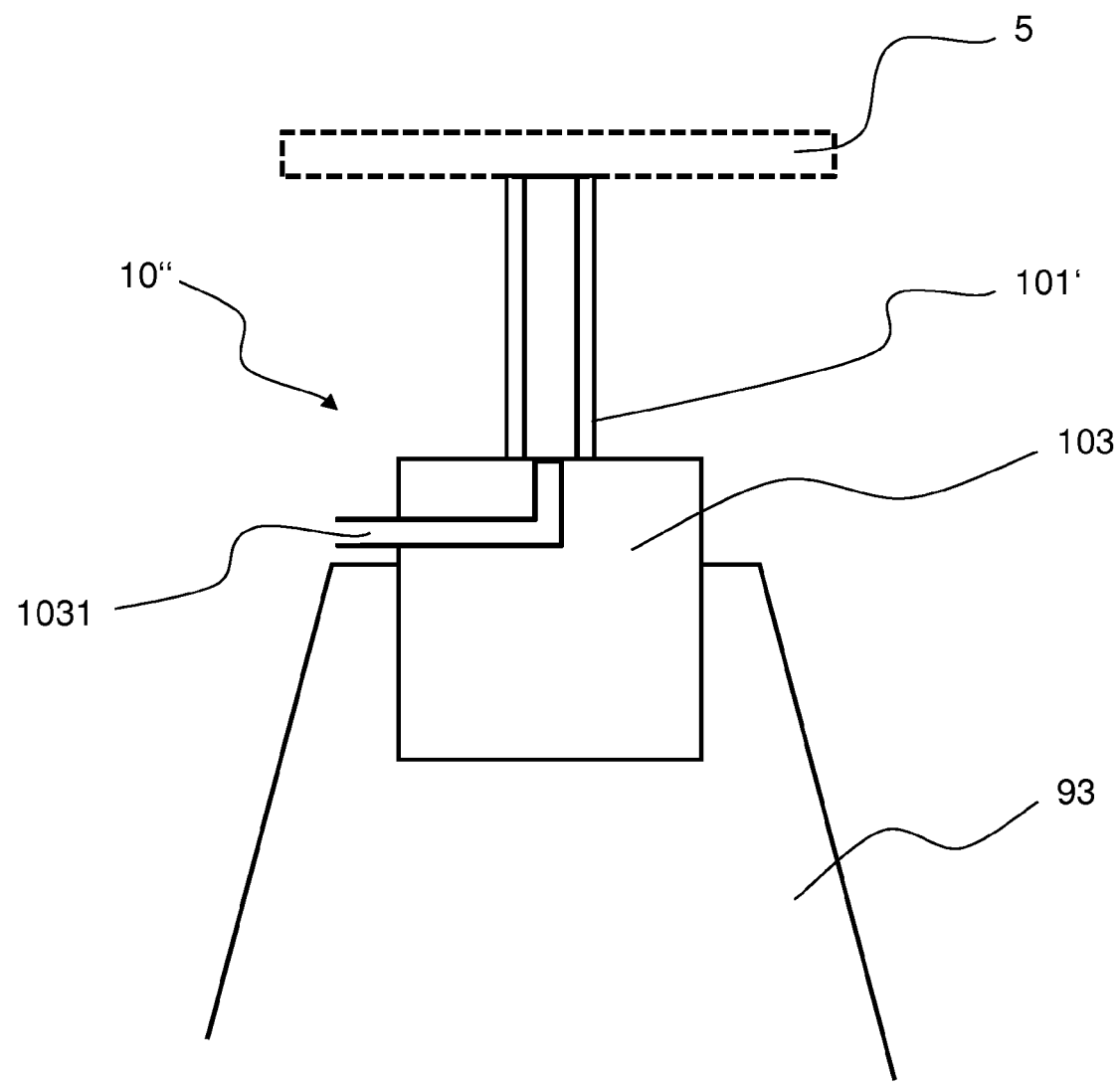
FIG. 4 shows a schematic of yet another preferred embodiment of a chip handling tool for use with the present invention.

FIG. 4 shows a schematic of yet another preferred embodiment of a chip handling tool 10" for use with the present invention. The chip handling tool 10' again comprises shank 103 by means of which it may e.g. be mounted to a chip handling unit, in particular the transfer unit 93. A hollow piezo electric actuator 101' is provided on the shank 103, so that a vacuum orifice is formed at an end of the hollow piezo electric actuator 101' remote from the shank 103. A vacuum supply channel 1031 is formed in the shank to allow for supplying vacuum to an inner side of hollow piezo electric actuator 101'. Preferably, a layer of soft material, e.g. rubber, is provided on the end of the hollow piezo electric actuator 101' remote from the shank 103 in order to prevent die 5 from coming into contact with a relatively hard material of the piezo electric actuator 101'.

As already mentioned, laser displacement meter 7 may be used to measure vibrations induced in die 5, e.g. by measuring displacements and/or deflections of die 5, e.g. as a function of time. The displacements and/or deflections may be measured at a single location, e.g. in just one corner of the die 5. Preferably, they are measured at two or multiple locations. This way it is ensured that damages may be detected irrespective of their location. It also allows to get an indication of where the damage might be located. This in turn is helpful as guidance for additional die inspection methods that may be applied.

Optical metrology based on interference may also be applied advantageously to measure displacements and/or deflections of die 5.

Based on an input to the piezo electric actuator 101 and measured displacement and/or deflection, one or more frequency response functions of the die 5 are calculated. Those contain amplitude and phase information on how the die 5 reacts to a vibration excitation. In general, the frequency response functions show various resonance peaks which correspond to natural eigenmodes of the die in that particular experimental setup.

When the die 5 is damaged, e.g. when cracks, splits, chip offs or other defects are present in the die, the frequency response functions show deviations when compared to reference frequency response functions of an undamaged, but otherwise identical die 5. In a damaged die 5, mechanical stiffness and mode shapes change, so that e.g. resonance shifts and resonance broadening due to additional damping may be expected. Thus, damaged dies 5 may be identified by comparing measured frequency response functions with the reference frequency function.

This is preferably accomplished by comparing response functions over a continuous range of frequencies, preferably in a subrange between 10 Hz and 100 kHz. Alternatively, it may be accomplished by just comparing one or more individual resonances with those from known good dies. Preferably, a sine-wave excitation is used, and the excitation frequency is swept slowly. However, a simultaneous excitation over a range of frequencies could also be used to advantage, in particular to allow for faster determination of the frequency response function. In particular, one could think of a white noise excitation to excite a wide spectrum of frequencies at once.

Instead of measuring vibrations induced in die 5 based on measurements of displacement and/or deflection by optical means as described above, an acoustic and/or ultrasonic receiver, e.g. a microphone or another piezo electric element, may preferably be employed. The vibration frequency response may thus be obtained directly without need measurements of displacement and/or deflection. Preferably, the vibrations induced in die 5 may also be measured by determining impedance or an impedance spectrum of the piezo electric actuator.

Based on a discrimination between damaged and undamaged dies 5 as described further above, exception handling controls may then allow for avoiding attaching of broken dies 5, and for removing them from the transfer unit 93.

Figure 5:
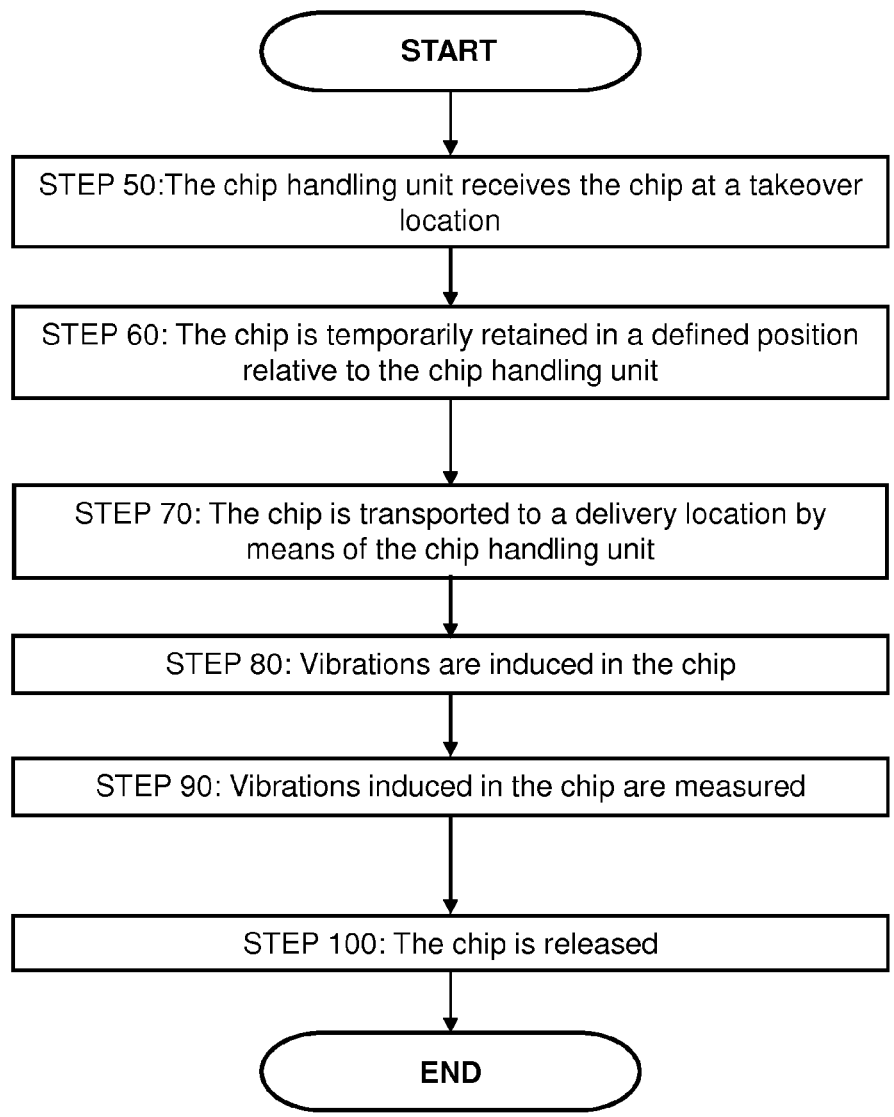
FIG. 5 shows a flow diagram illustrating a chip handling process in accordance with an exemplary embodiment of the present invention.

FIG. 5 shows a flow diagram in accordance with certain exemplary embodiments of the present invention. As is understood by those skilled in the art, certain steps included in the flow diagram may be omitted; certain additional steps may be added, and the order of the steps may be altered from the order illustrated.

In the description so far, die 5 was retained in a defined position relative to the transfer unit 93 by means of vacuum suction. This implies that the die 5 is sucked against some kind of support surface in which one or more vacuum orifices are formed, or which is defined by one or more vacuum orifices. Preferably, the die 5 may also be retained in position by a contactless setup, for example by a combination of attractive, e.g. electrostatic, forces and repulsive forces, e.g. due a flow of compressed air, to which the die may be exposed in close proximity to a work surface of an adequately designed chip handling tool.

Although the invention is illustrated and described herein with reference to specific embodiments, the invention is not intended to be limited to the details shown. Rather, various modifications may be made in the details within the scope and range of equivalents of the claims and without departing from the invention.

In particular, although the invention was described above with respect to semiconductor dies, it may be used for any kind of chip, including any essentially a flat slab of material or materials that is picked from any kind of supply carrier, in particular a tape or belt, and placed onto a target location, in particular on a chip, substrate, tape, belt or a storage means.

What is claimed:

1. A chip handling apparatus comprising
   a) a chip supply station,
   b) a chip mounting station,
   c) one or more chip handling units configured to pick a chip from the chip supply station, transport the chip to the chip mounting station, and place the chip at a mounting location,
      wherein each chip handling unit is configured to temporarily retain the chip in a defined position relative to said chip handling unit,
   d) means for inducing vibrations, in particular sonic and/or ultrasonic vibrations, in the chip when retained by one of the chip handling units; and
   e) means for measuring the vibrations induced in the chip such that at least one measured frequency response function is configured for comparison to at least one reference frequency response function to determine whether the chip is damaged.

2. The chip handling apparatus according to claim 1, further comprising discrimination means configured to determine whether the chip is damaged based upon a measurement of the vibrations induced in the chip.

3. The chip handling apparatus according to claim 1 wherein the one or more chip handling units includes a first chip handling unit for picking the chip from the chip supply station, and a second chip handling unit for placing the chip onto the chip mounting location, and wherein the first chip handling unit is configured to hand the chip to the second chip handling unit at a first hand over location.

4. The chip handling apparatus according to claim 1 wherein the one or more chip handling units includes a first chip handling unit for picking the chip from the chip supply station, a second chip handling unit for placing the chip onto the mounting location, and a third chip handling unit configured to receive the chip from the first chip handling unit, and hand it to the second chip handling unit.

5. The chip handling apparatus according to claim 4, wherein the means for inducing vibrations in the chip are configured to induce vibrations when the chip is retained by the second chip handling unit.

6. A chip handling unit configured to receive a chip at a takeover location and to hand over said chip to a delivery location, said chip handling unit comprising:
 a) means for temporarily retaining the chip in a defined position relative to the chip handling unit, and
 b) means for inducing vibrations, in particular sonic and/or ultrasonic vibrations, in the chip, such that at least one measured frequency response function is configured for comparison to at least one reference frequency response function to determine whether the chip is damaged.

7. A chip handling process comprising the steps of:
 a) receiving a chip at a takeover location by means of a chip handling unit,
 b) temporarily retaining the chip in a defined position relative to the chip handling unit,
 c) transporting the chip to a delivery location,
 d) subsequently releasing the chip,
  wherein between steps a) and d), vibrations are induced in the chip, and
  the vibrations induced in the chip are measured, and wherein at least one measured frequency response function is configured for comparison to at least one reference frequency response function to determine whether the chip is damaged.

8. The chip handling process according to claim 7, wherein the vibrations induced in the chip are sonic and/or ultrasonic vibrations.

9. The chip handling process according to claim 7, wherein at the delivery location, the chip is placed onto a substrate or onto another chip.

10. The chip handling process according to claim 7, wherein at the delivery location, the chip is handed to a place unit.

11. A chip handling process comprising the steps of:
 a) picking a chip from a supply station,
 b) transporting the chip to a mounting station by means of at least one chip handling unit, said at least one chip handling unit being configured to temporarily retain the chip in a defined position relative to the chip handling unit, and
 c) placing the chip onto a mounting location,
  wherein in step b), vibrations are induced in the chip, and
 d) the vibrations induced in the chip are measured, and wherein at least one measured frequency response function is configured for comparison to at least one reference frequency response function to determine whether the chip is damaged.

12. The chip handling process according to claim 11, wherein the vibrations induced in the chip are sonic and/or ultrasonic vibrations.

13. The chip handling process according to claim 11 further comprising the step of determining whether the chip is damaged based upon an analysis of the vibrations measured.

* * * * *